(12) United States Patent
Kitajo et al.

(10) Patent No.: US 10,835,029 B2
(45) Date of Patent: Nov. 17, 2020

(54) TOOTHBRUSH

(71) Applicant: OMRON HEALTHCARE Co., Ltd., Kyoto (JP)

(72) Inventors: Kotaro Kitajo, Kyoto (JP); Hideyuki Yamashita, Kyoto (JP); Yasuhiro Kawabata, Kyoto (JP); Katsunori Kondo, Kyoto (JP); Hideaki Yoshida, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 182 days.

(21) Appl. No.: 16/165,177

(22) Filed: Oct. 19, 2018

(65) Prior Publication Data
US 2019/0045917 A1    Feb. 14, 2019

Related U.S. Application Data

(63) Continuation of application No. PCT/JP2017/015529, filed on Apr. 18, 2017.

(30) Foreign Application Priority Data

Apr. 22, 2016  (JP) .................................. 2016-086523

(51) Int. Cl.
*A61C 17/22* (2006.01)
*A46B 15/00* (2006.01)
(Continued)

(52) U.S. Cl.
CPC ........ *A46B 15/0034* (2013.01); *A46B 5/0095* (2013.01); *A46B 9/04* (2013.01);
(Continued)

(58) Field of Classification Search
CPC .......... A61C 17/22; A61C 17/34; A46B 13/02
See application file for complete search history.

(56) References Cited

U.S. PATENT DOCUMENTS 3,369,265 A * 2/1968 Halberstadt ............ A61C 17/32
    15/22.1
9,597,169 B2 * 3/2017 Hall ....................... A46B 7/042
(Continued)

FOREIGN PATENT DOCUMENTS

JP    H7-148020 A      6/1995
JP    2009-022697 A    2/2009
(Continued)

OTHER PUBLICATIONS

International Search Report dated May 30, 2017 of corresponding International Application No. PCT/JP2017/015529; 2 pgs.

*Primary Examiner* — Michael D Jennings
(74) *Attorney, Agent, or Firm* — Maier & Maier, PLLC

(57) ABSTRACT

A toothbrush including a main body having a shape which is narrow and long in one direction; and a brush member which has a cylindrical shape and which is mounted to an end section in the lengthwise direction of the main body. The brush member includes: a head part which has a raised surface, on which bristles are erected, along the lengthwise direction of the main body to which the brush member is mounted; and a neck part which is mounted by engaging with the periphery of the end section of the main body. In the head part, a back surface on the opposite side of the raised surface is opened, and the neck part is provided with a detachment prevention mechanism that prevents the end of the main body to which the brush member is mounted from detaching.

5 Claims, 11 Drawing Sheets

(51) Int. Cl.
  *A61C 17/34* (2006.01)
  *A46B 5/00* (2006.01)
  *A46B 9/04* (2006.01)
  *A61B 5/00* (2006.01)

(52) U.S. Cl.
  CPC ............ *A61C 17/22* (2013.01); *A61C 17/222* (2013.01); *A61C 17/3481* (2013.01); *A61B 5/0088* (2013.01)

(56) References Cited

U.S. PATENT DOCUMENTS

| | | | |
|---|---|---|---|
| 9,775,693 B2 * | 10/2017 | Fattori | ................. A61C 17/222 |
| 2014/0199651 A1 | 7/2014 | Adachi | |
| 2015/0020325 A1 | 1/2015 | Yoshida et al. | |

FOREIGN PATENT DOCUMENTS

| | | |
|---|---|---|
| JP | 2009-216497 A | 9/2009 |
| JP | 2009-273621 A | 11/2009 |
| JP | 2013-042906 A | 3/2013 |
| JP | 2015-507501 A | 3/2015 |

* cited by examiner

TOOTHBRUSH

CROSS-REFERENCE TO RELATED APPLICATIONS

This is a continuation application of International Application No. PCT/JP2017/015529, with an International filing date of Apr. 18, 2017, which claims priority of Japanese Patent Application No. 2016-086523 filed on Apr. 22, 2016, the entire content of which is hereby incorporated by reference.

FIELD

The present invention relates to a toothbrush, and more particularly to a toothbrush including a main body having a shape elongated in one direction, and a replacement brush having a cylindrical shape and attached to an end portion of the main body in its longitudinal direction.

BACKGROUND

Conventionally, there is known this type of toothbrush, as disclosed in Patent Literature 1 (JP 2009-273621 A), which includes a head section having bristles erected, and a raised surface (bristle holding surface) provided in its substantially central region with a light emitting element for emitting light to a tooth surface (e.g., refer to FIG. 7 of Patent Literature 1).

SUMMARY

However, the toothbrush of Patent Literature 1 requires a space for housing the light emitting element in the substantially central region of the head section. This causes a problem that the head section is increased in width and thickness to cause its insertion into a mouth to be difficult.

Thus, it is an object of the present invention to provide a toothbrush having a head section that is easily inserted into a mouth even when the head section has a light emitting element.

To solve the above problem, a toothbrush of the present disclosure comprises:

a main body having a shape elongated in one direction; and a replacement brush having a cylindrical shape and attached to an end portion of the main body in a longitudinal direction, the end portion of the main body having a stem projecting in the longitudinal direction, the replacement brush including a head section having a raised surface provided with bristles erected, and a neck section that is fitted and attached around the stem of the main body, along the longitudinal direction of the main body to be attached, wherein the head section is opened in a back side opposite to the raised surface to form a cavity, and the cavity communicates with a space in the neck section, the head section includes an outer body that has a wall constituting the raised surface, and sidewalls extending from both respective edges of the wall toward the back side, the stem extends to a back surface of the wall constituting the raised surface through a space inside the neck section when the replacement brush is attached to the end portion of the main body, each of the sidewalls of the head section has a leading end provided with a holding portion for holding the stem of the main body, and the neck section includes a disengaging prevention structure for preventing the end portion attached of the main body from disengaging.

The description of "the replacement brush", wherein "the head section is opened in a back side opposite to the raised surface", includes the replacement brush having a plate-like shape. In the present specification, the "end portion" is not limited to each end itself, and may indicate a portion within a certain range.

In another aspect, a toothbrush of the present disclosure comprises:

a main body having a shape elongated in one direction; and a replacement brush having a cylindrical shape and attached to an end portion of the main body in a longitudinal direction, the replacement brush including a head section having a raised surface provided with bristles erected, and a neck section that is fitted and attached around the end portion of the main body, along the longitudinal direction of the main body to be attached, wherein the head section is opened in a back side opposite to the raised surface, a light emitting part that is provided in the end portion of the main body to emit light to a tooth surface through a specific region in the raised surface; and a positioning structure for positioning the light emitting part in the end portion of the main body and the specific region so as to overlap with each other in the longitudinal direction of the main body when the replacement brush is attached to the main body.

BRIEF DESCRIPTION OF DRAWINGS

The present invention will become more fully understood from the detailed description given hereinbelow and the accompanying drawings which are given by way of illustration only, and thus are not limitative of the present invention, and wherein.

DETAILED DESCRIPTION

Hereinafter, an embodiment of the present invention will be described in detail with reference to the drawings.

(Embodiment)
(Structure)

Figure 1:
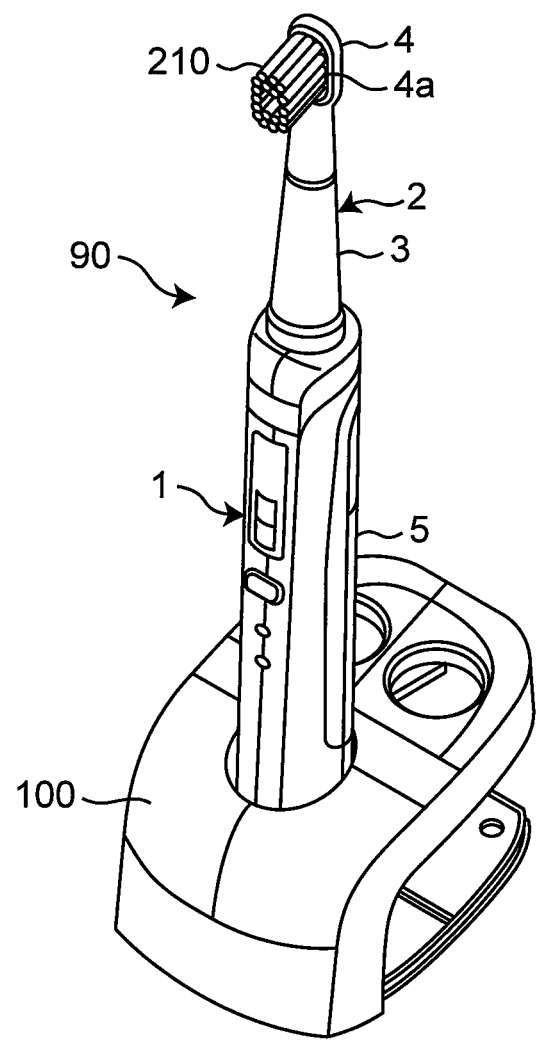
FIG. 1 is a perspective view illustrating an appearance of a toothbrush according to an embodiment of the present invention (the whole is indicated by a reference numeral 90).
Figure 2A:
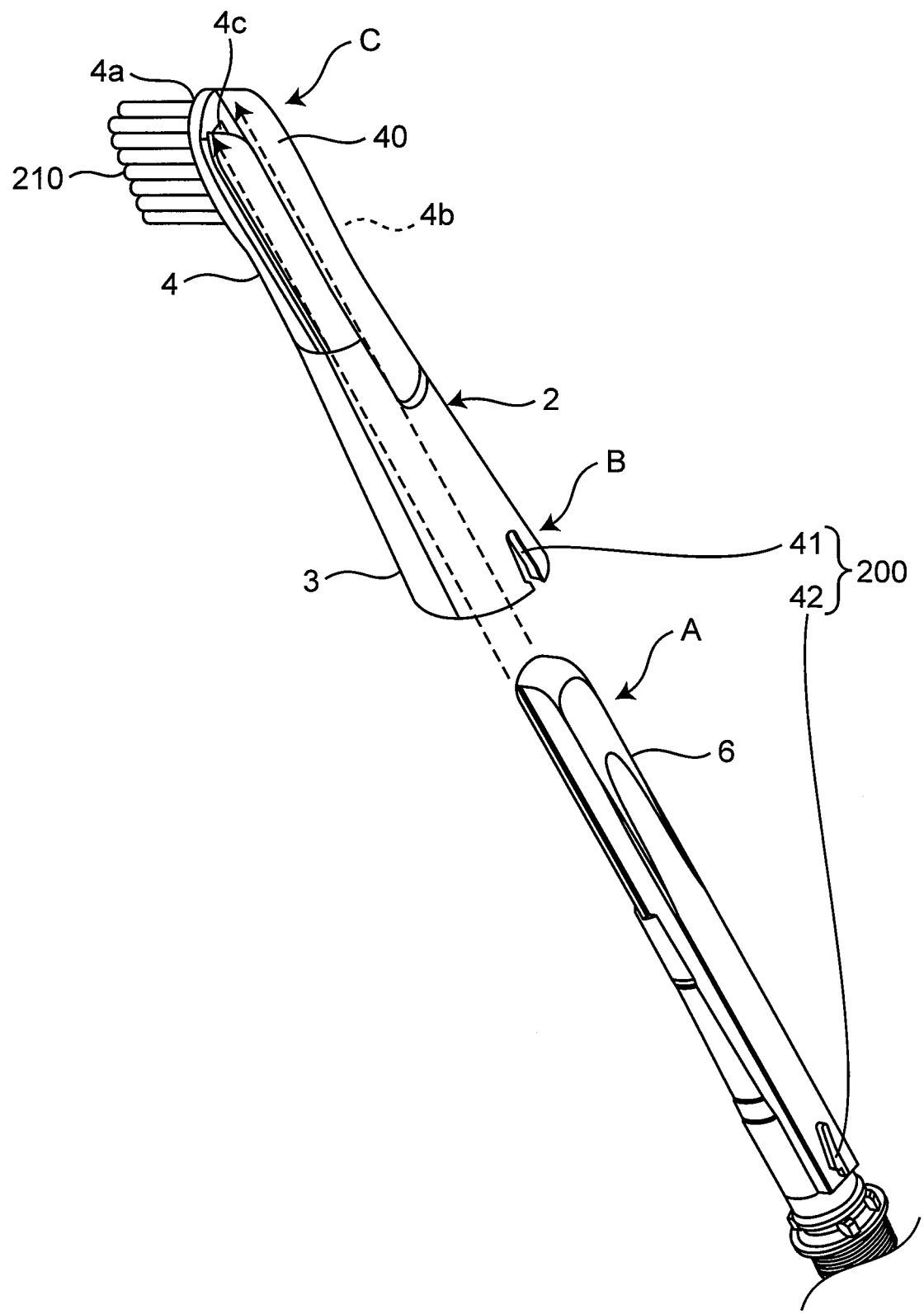
FIG. 2A is a perspective view illustrating a state when a stem 6 of a main body 1 of FIG. 1 is inserted into a brush member 2.
Figure 2B:
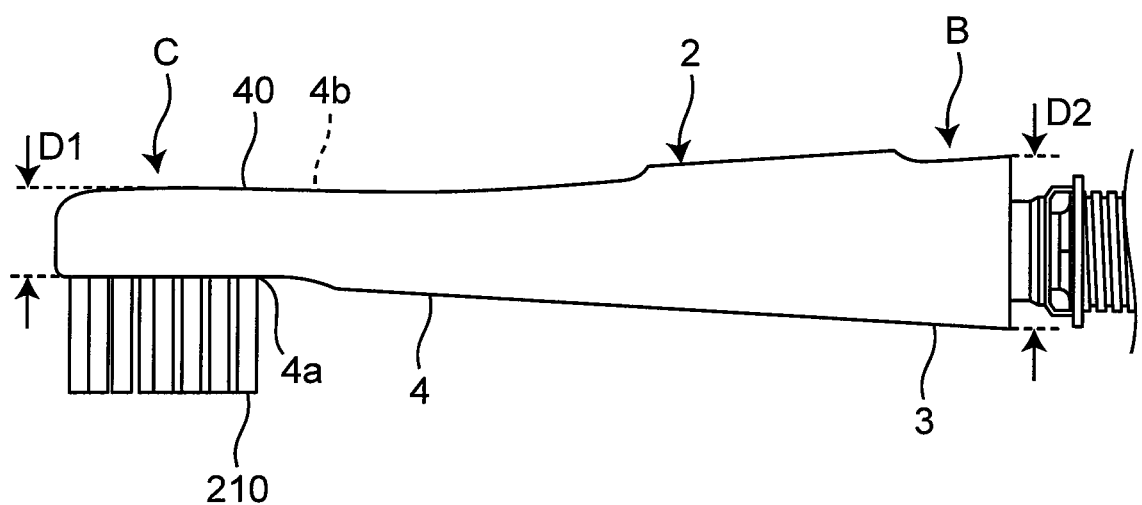
FIG. 2B is a side view of the brush member 2 of FIG. 1.

FIG. 1 is a perspective view illustrating an appearance of a toothbrush according to the embodiment of the present invention (the whole is indicated by a reference numeral 90). FIG. 2A is a perspective view illustrating a state when a stem 6 of a main body 1 of FIG. 1 is inserted into a brush member 2. FIG. 2B is a side view of the brush member 2 of FIG. 1. As illustrated in FIG. 1, the toothbrush 90 includes a main body 1 having a shape elongated in one direction, and a brush member 2 that is a replacement brush having a cylindrical shape and attached to an end portion of the main body 1 in its longitudinal direction. The brush member 2 is a consumable part, and thus is configured to be detachable from a grip section 5 so as to be able to be replaced with a new one. FIG. 1 illustrates a charger 100.

As illustrated in FIGS. 1, 2A, and 2B, the main body 1 includes the grip section 5 to be grasped by hand. The brush member 2 includes a head section 4 having bristles 210 erected, and a neck section 3 for connecting the head section 4 and the grip section 5. Here, the head section 4 and the neck section 3 are integrally formed as a brush member 2 detachable from the grip section 5.

As illustrated in FIGS. 2A and 2B, the head section 4 is provided with a cavity 40 by opening its back side 4b opposite to a raised surface 4a, where provided with the bristles 210 erected. That is, the cavity 40 communicates with a space inside the brush member 2 in a cylindrical shape. When the head section 4 has a cylindrical shape with a back side 4b that is not opened, the brush member 2 has a leading end portion C and the other end portion B each of which has an almost identical thickness. In contrast, the present invention allows the leading end portion C excluding bristles 210 of the brush member 2 to have a thickness D1 less than a thickness D2 of the other end portion B of the brush member 2 when the brush member 2 is attached to the main body 1. This enables the leading end portion C to have a thickness less than that of a conventional one, so that a user can easily insert the head section 4 of the toothbrush 90 into its mouth, and brushing of its back teeth can be facilitated.

In addition, the back side 4b opposite to the raised surface 4a, where provided with the bristles 210, is opened, so that the head section 4 has a volume less than that of the head section 4 having a cylindrical shape. As a result, material costs can be reduced compared with conventional material costs.

The head section 4 of the brush member 2 is opened to form a cavity 40, and this cavity 40 communicates with a space in the neck section 3, so that water can pass through the inside of the brush member 2 having a cylindrical shape through the head section 4 and the neck section 3. Thus, as compared with the case that the head section 4 is not opened, the inside of the brush member 2 can be easily cleaned.

In addition, the head section 4 of the brush member 2 is opened, so that the brush member 2 is reduced in weight to enable reduction in power consumption by efficiently transmitting output of a motor to the bristles 210 of the brush member 2.

As illustrated in FIGS. 1 and 2A, the bristles are omitted in a specific region 4c in a substantially central portion in the raised surface 4a of the head section 4. As described below with reference to FIG. 5, a light emitting part 50 and the light receiving part 51 are disposed side by side inside the raised surface 4a of the head section 4, corresponding to the specific region 4c.

As illustrated in FIG. 2A, the neck section 3 is provided with a disengaging prevention structure 200 for preventing the brush member 2 from disengaging from the main body 1 when the brush member 2 is attached to the main body 1. The disengaging prevention structure 200 includes a cutout portion 41 provided at the end portion B of the cylindrical peripheral wall of the neck section 3, on a side facing the main body 1, and a locking protrusion 42 that is provided on a side surface of the main body 1 and that can be fitted into the cutout portion 41. This enables the brush member 2 to be reliably fixed to the main body 1 by fitting the cutout portion 41 and the locking protrusion 42 to each other when the brush member 2 is attached to the main body 1. As described above, the brush member 2 can be reliably fixed to the main body 1, so that vibration from the main body 1 can be efficiently and effectively transmitted to a brush portion of the brush member 2.

While the cutout portion 41 is provided in the back side opposite to the raised surface 4a provided with the bristles 210, on a side facing the main body 1, in the present embodiment, the present invention is not limited thereto. For example, the cutout portion 41 may be provided at an end portion in the peripheral wall other than the back side opposite to the raised surface 4a, on the side facing the main body 1. In even this case, a similar advantageous effect to that of the present embodiment can be obtained.

Next, the disengaging prevention structure 200 will be described below.

Figure 3A:
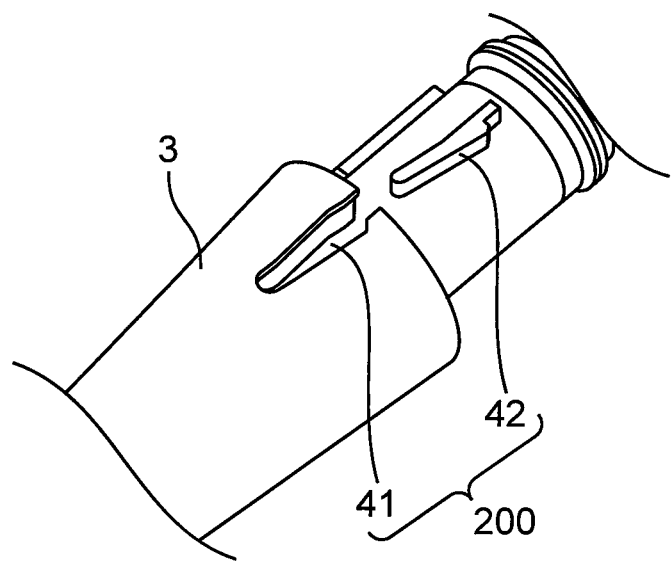
FIG. 3A is an enlarged perspective view for illustrating a first state of operation of a disengaging prevention structure 200 in FIG. 2A.
Figure 3B:
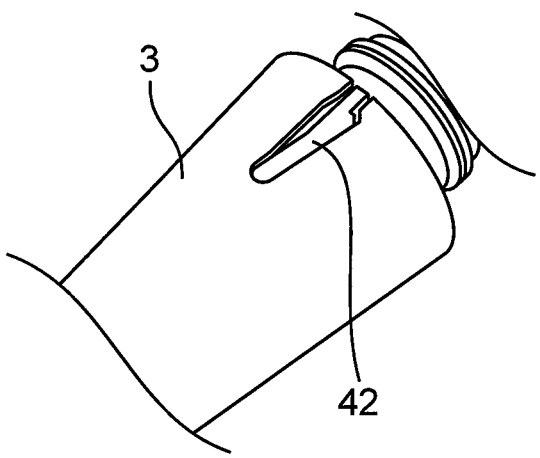
FIG. 3B is an enlarged perspective view for illustrating a second state of operation of the disengaging prevention structure 200 in FIG. 2A.
Figure 4A:
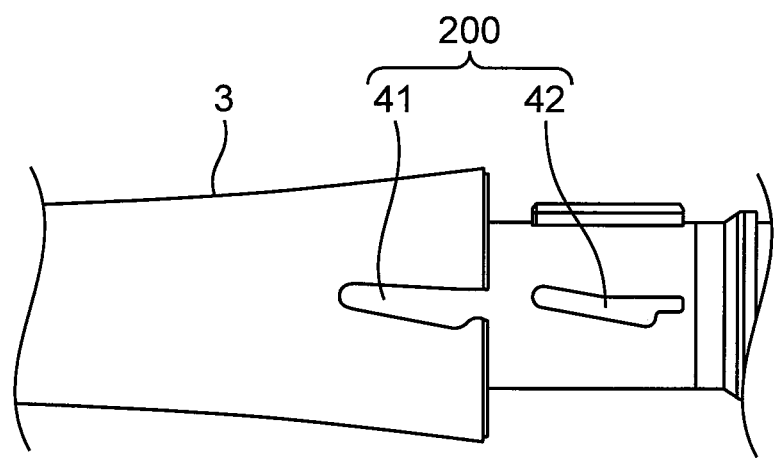
FIG. 4A is a top view of FIG. 3A.
Figure 4B:
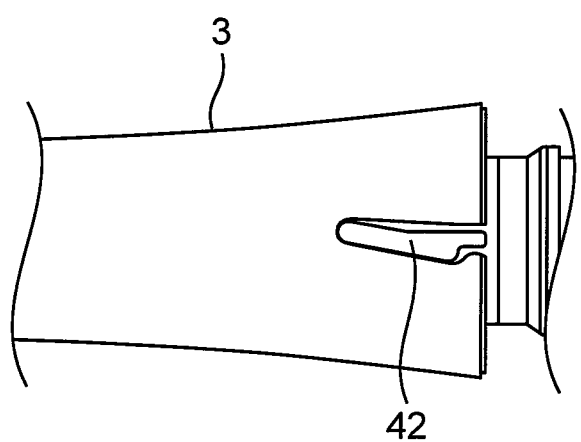
FIG. 4B is a top view of FIG. 3B.

FIGS. 3A and 3B are each an enlarged perspective view for illustrating operation of the disengaging prevention structure 200 in FIG. 2A. FIG. 4A is a top view of FIG. 3A, and FIG. 4B is a top view of FIG. 3B. FIGS. 3A and 4A each illustrate a state just before the locking protrusion 42 provided in the main body 1 is fitted into the cutout portion 41 provided in the end portion B of the brush member 2 after the stem 6 of the main body 1 is inserted into the brush member 2 from the end portion B thereof. FIGS. 3B and 4B each illustrate a state where the locking protrusion 42 provided in the main body 1 is fitted in the cutout portion 41 provided in the end portion B of the brush member 2. This state enables the brush member 2 to be prevented from disengaging from the main body 1 even while a user is brushing its teeth.

Figure 5:
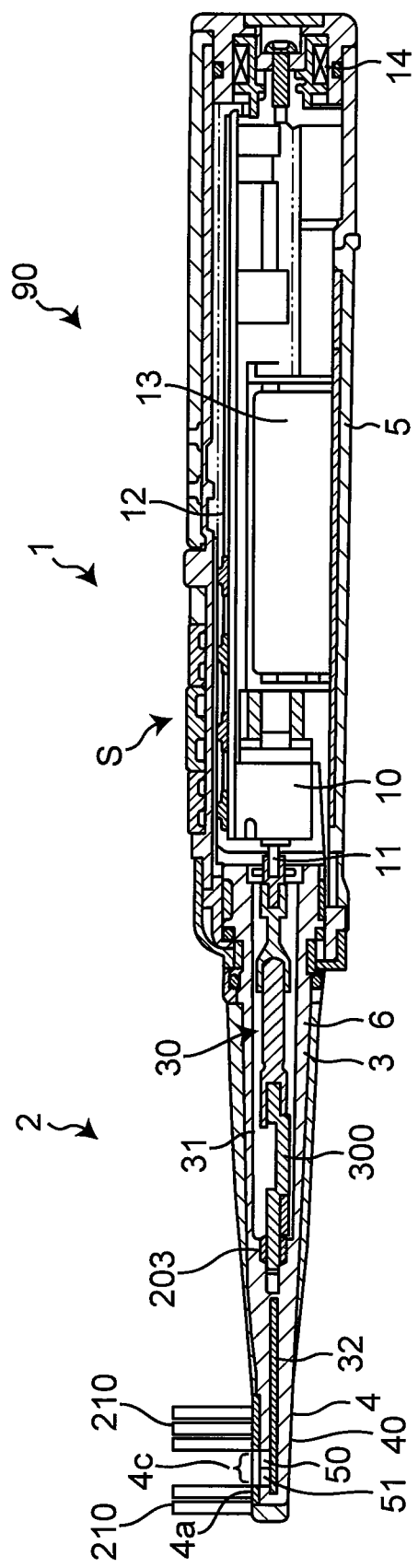
FIG. 5 is a longitudinal sectional view of the toothbrush 90 of FIG. 1 taken along its longitudinal direction.

FIG. 5 illustrates a longitudinal sectional view of the toothbrush 90 taken along its longitudinal direction. The grip section 5 has the stem 6 provided so as to protrude from an outer body of the grip section 5 toward the neck section 3. The stem 6 has a cylindrical shape with a leading end closed. In this example, the neck section 3 of the brush member 2 is fitted and attached so as to cover the stem 6. On the surface (raised surface) 4a on one side of the head section 4 of the brush member 2, the bristles (brushes) 210 are erected so as to protrude from the raised surface 4a by about 10 mm to 12 mm by implantation in this example. Besides the implantation, the bristles 210 may be welded or bonded.

The grip section 5 of the main body 1 is provided on its outer surface with a switch S for turning on/off a power supply. The grip section 5 is also provided in its inside with a motor 10 as a drive source, a drive circuit 12, a rechargeable battery 13 as a power supply part, a charging coil 14, and the like. When the rechargeable battery 13 is recharged, charging can be performed in a noncontact manner by electromagnetic induction merely by placing the main body 1 on the charger 100 illustrated in FIG. 1A.

As illustrated in FIG. 5, the stem 6 is provided in its inside with a bearing 203. Into the bearing 203, a leading end of an eccentric shaft 30 connected to a rotating shaft 11 of the motor 10 is inserted. The eccentric shaft 30 has a weight 300 near the bearing 203, and the center of gravity of the eccentric shaft 30 is displaced from the center of rotation thereof. When the drive circuit 12 supplies a drive signal (e.g., a pulse width modulated signal) corresponding to an operation mode to the motor 10 to rotate the rotating shaft 11 of the motor 10, the eccentric shaft 30 is also rotated with the rotation of the rotating shaft 11. The eccentric shaft 30 has the center of gravity displaced from the center of rotation thereof, and thus moves so as to turn around the rotation center. This causes the leading end of the eccentric shaft 30 to repeatedly collide against an inner wall of the bearing 203, thereby vibrating (moving) the bristles 210 at a high speed.

The bristles are omitted in the specific region 4c in the substantially central portion in the raised surface 4a of the head section 4. The light emitting part 50 and the light receiving part 51 are disposed side by side inside the raised surface 4a of the head section 4, corresponding to the specific region 4c. That is, the light emitting part 50 and the light receiving part 51 are provided in an end portion A of the main body 1. The raised surface 4a of the head section 4 has a portion (outer body) including at least the specific region 4c that is made of a transparent resin material having a thickness of about 1 mm to 3 mm.

The light emitting part 50 in FIG. 5 includes a light emitting diode that emits excitation light having a peak wavelength corresponding to ultraviolet or blue toward a tooth surface through the specific region 4c. In this example, the light emitting diode is an LED (model No. SM0603UV-405) manufactured by Bivar Inc., and generates light having a peak wavelength of 405 nm.

The light receiving part 51 in FIG. 5 includes an optical filter member that receives radiation light from the tooth surface through the specific region 4c and allows spectral components of the radiation light, only within a predetermined wavelength range, to be transmitted therethrough, and a photodiode that receives the spectral components only within the predetermined wavelength range that has transmitted the optical filter member. In this example, the optical filter member is a long pass filter (model No. LV0610) manufactured by Asahi Spectra Co., Ltd., and allows light having a wavelength of 610 nm or more as the above predetermined wavelength region to pass therethrough, while blocking light having a wavelength of less than 610 nm (high pass type). In addition, the photodiode is composed of a photo diode (PD) (model No. NJL6401R-3) manufactured by New Japan Radio Co., Ltd., in this example. The light receiving part 51 may be composed of a phototransistor rather than a photodiode.

The light emitting part 50 and the light receiving part 51 are electrically connected to the drive circuit 12 via a lead wire 31 and a rigid flexible board 32 illustrated in FIG. 5, respectively.

Figure 6:
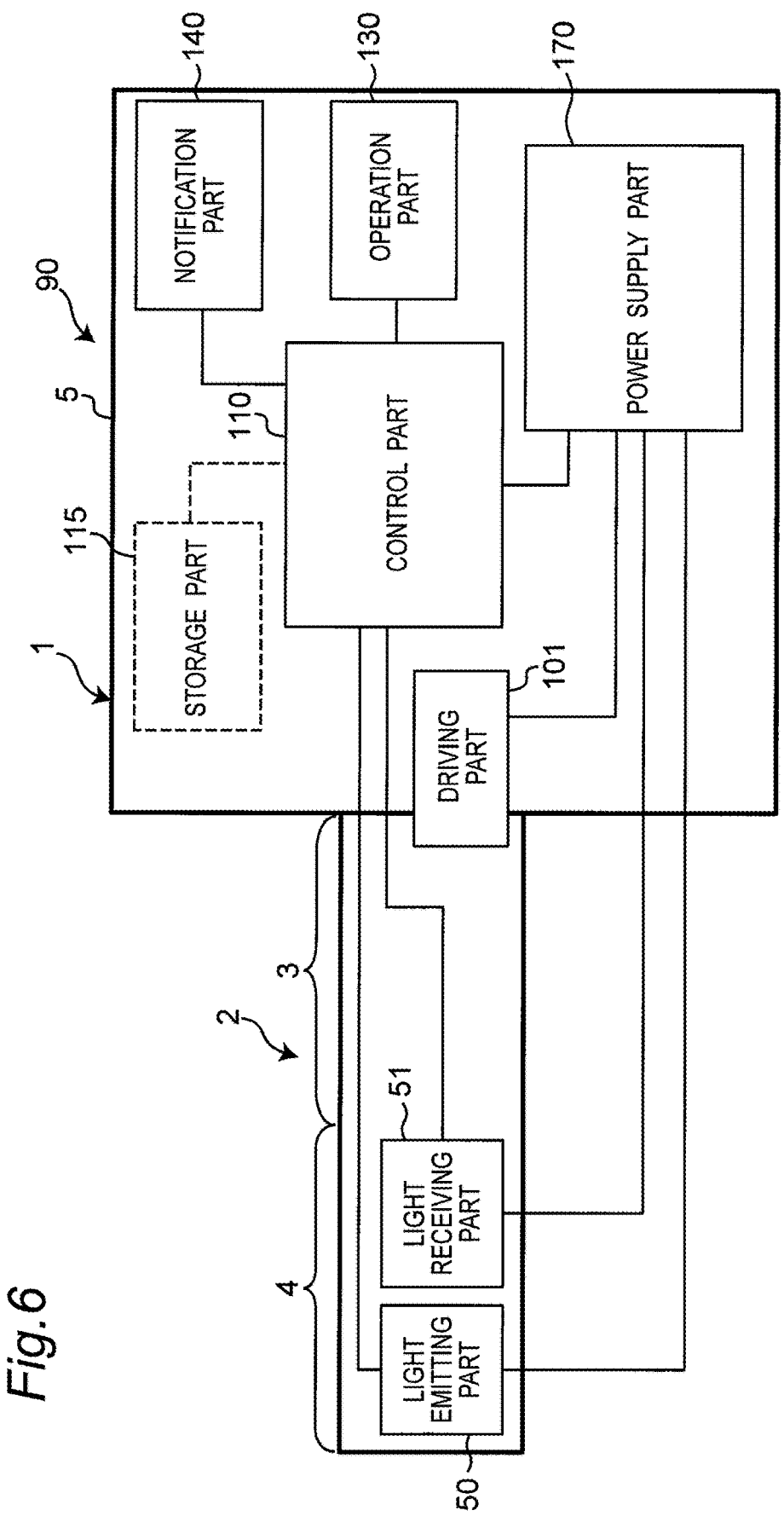
FIG. 6 is a block diagram schematically illustrating a configuration of a control system of the toothbrush 90 of FIG. 1.

FIG. 6 illustrates a block configuration of a control system of the toothbrush 90. The grip section 5 of the toothbrush 90 is provided in its inside with a control part 110 constituting the drive circuit 12 as above, a storage part 115, an operation part 130, a notification part 140, and a power supply part 170. In addition, a driving part 101 represents the motor 10, the rotating shaft 11, the eccentric shaft 30, bearing 203, and the weight 300, which are described above.

The control part 110 includes a central processing unit (CPU) operated by software, and not only causes the motor 10 to be driven, but also executes a process for determining whether dental plaque (or calculus) exists on a tooth surface 99a, and other various processes.

The operation part 130 includes the switch S described above, and works when a user turns on/off a power source of the toothbrush 90.

In this example, the storage part 115 includes an electrically rewritable nonvolatile memory (EEPROM) that can non-transitorily store data. The storage part 115 stores a control program for controlling the control part 110.

In this example, the notification part 140 includes a buzzer, and notifies whether dental plaque (or calculus) exists by sounding a buzzer sound. Instead of or in addition to the buzzer, an LED lamp may be provided to notify whether dental plaque (or calculus) exists by turning on or blinking the LED lamp.

The power supply part 170 includes the rechargeable battery 13 described above, and supplies electric power (DC 2.4 V in this example) to the parts in the toothbrush 90.

(Operation)

The toothbrush 90 is configured such that when a user turns on the switch S, the control part 110 causes the motor 10 to rotate to vibrate (move) the bristles 210 at a high speed. In addition, the control part 110 serves as a dental plaque detector to perform processing for determining whether dental plaque (or dental calculus) exists on the tooth surface 99a, as described below.

Specifically, the control part 110 turns on the light emitting part 50 so that the light emitting part 50 emits light toward the tooth surface 99a through the specific region 4c. Accordingly, radiation light is emitted from the tooth surface 99a. The radiation light is received by the light receiving part 51 through the specific region 4c. The output of the light receiving part 51 is input to the control part 110.

Subsequently, the control part 110 determines whether dental plaque exists on the tooth surface 99a on the basis of the output of the light receiving part 51 using a publicly known method for detecting unique fluorescence of the dental plaque, as disclosed in Patent Literature 2 (JP 2002-522102 A). This toothbrush is configured such that the light emitting part 50 emits light toward the tooth surface in contact with the tips of the respective bristles 210, and the light receiving part 51 receives the radiation light from the tooth surface. Then, it is determined whether dental plaque exists on the tooth surface in accordance with intensity of the radiation light received by the light receiving part 51.

After that, the control part 110 causes the notification part 140 to notify whether dental plaque (or calculus) exists by sounding a buzzer sound, in this example.

As a result, a user can know a determination result of whether dental plaque (or calculus) exists while brushing its teeth. This enables eliminating an optical fiber, wiring, or the like extending from the toothbrush 90 to the outside. In such a case, when a user brushes its teeth with the toothbrush 90, the user can easily brush the teeth without any obstacle.

(Modification 1)

Figure 7A:
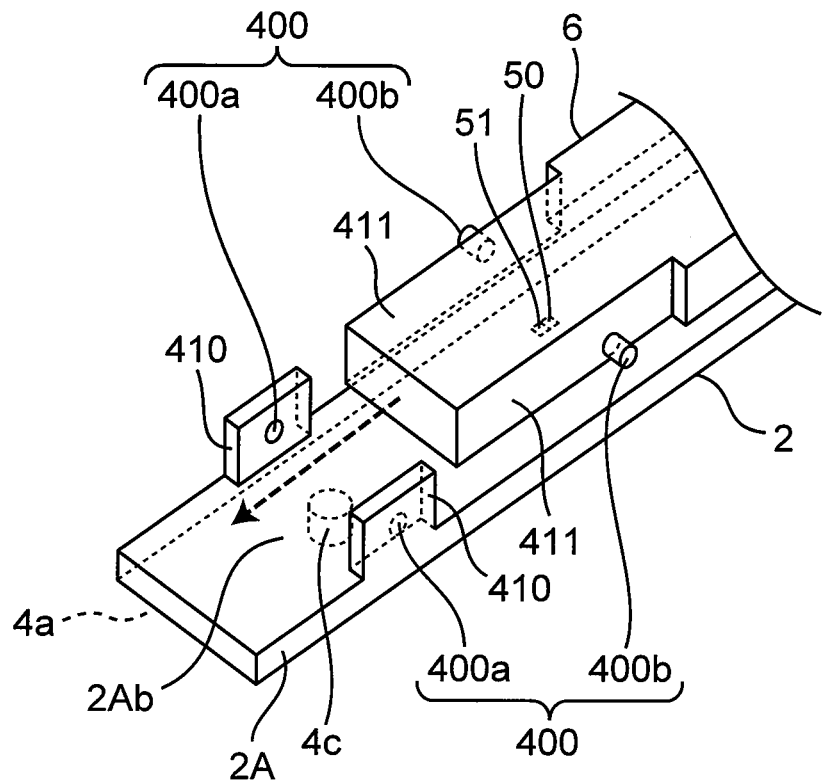
FIG. 7A is a schematic view for illustrating a first state of operation of a positioning structure 400 according to a modification 1 of the embodiment of the present invention.
Figure 8A:
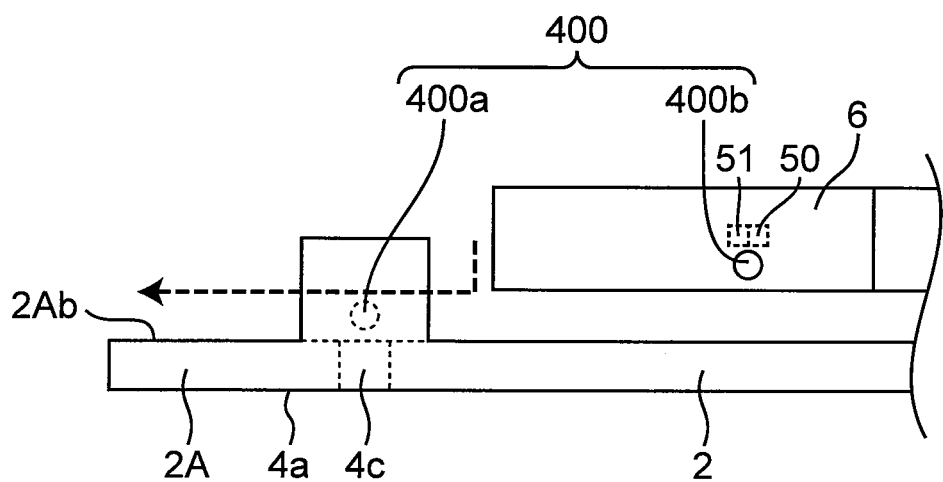
FIG. 8A is a side view of FIG. 7A.

The embodiment described above is configured such that when the brush member 2 is attached to the main body 1, the light emitting part 50 and the light receiving part 51, provided on the main body 1, and the specific region 4c are positioned so as to overlap with each other in the longitudinal direction of the main body 1. Thus, a positioning structure 400 as illustrated in FIGS. 7A and 8A may be further provided. This structure causes the light emitting part 50 and the light receiving part 51 to be less likely to be displaced from the specific region 4c.

Figure 7B:
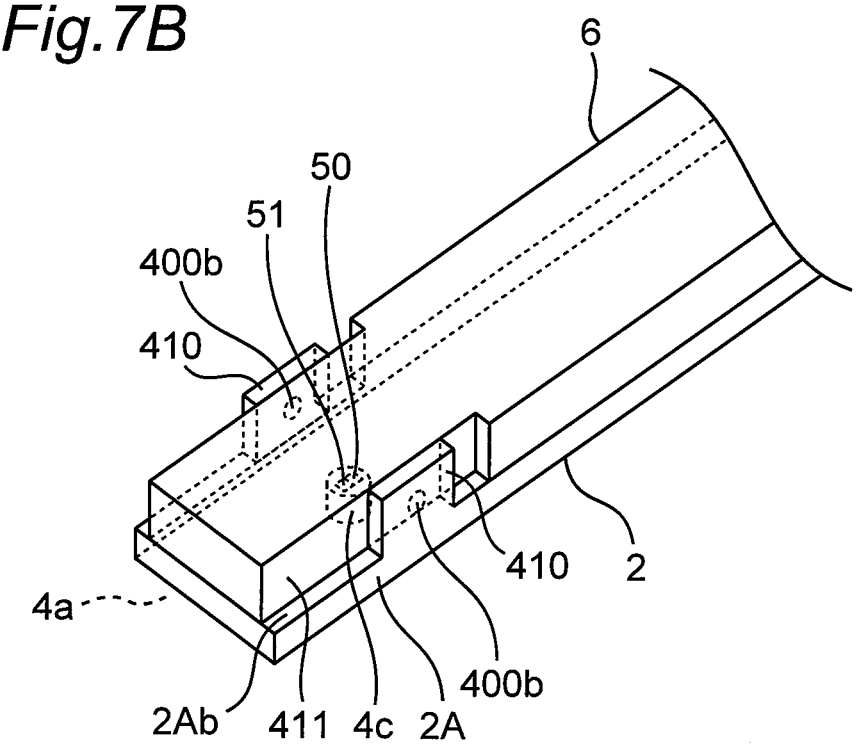
FIG. 7B is a schematic view for illustrating a second state of operation of the positioning structure 400 according to the modification 1 of the embodiment of the present invention.
Figure 8B:
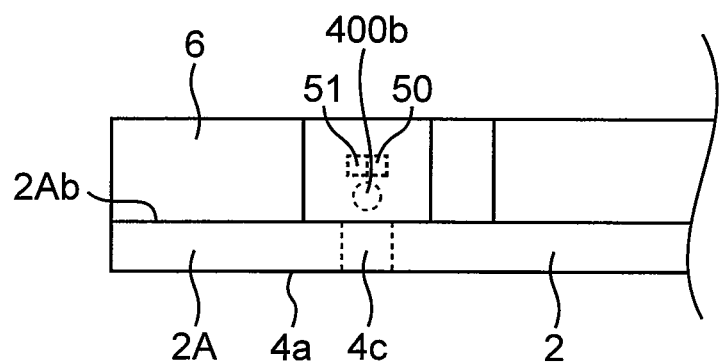
FIG. 8B is a side view of FIG. 7B.

FIGS. 7A and 7B are each a schematic view for illustrating operation of the positioning structure 400 according to the modification 1 of the embodiment of the present invention. FIG. 8A is a side view of FIG. 7A, and FIG. 8B is a side view of FIG. 7B. The positioning structure 400 includes first positioning elements (first recesses 400a) provided in a surface opposite to the raised surface 4a, and second positioning elements (first protrusions 400b) provided in a leading end portion of the main body 1, and is configured such that the first positioning elements can engage with the respective second positioning elements. This allows the brush member 2 to be more easily fitted onto the main body 1 when the light emitting part 50 and the light receiving part 51 are positioned in the specific region 4c, thereby further facilitating attachment of the brush member 2 to the main body 1.

As illustrated in FIG. 7A, the head section 4 includes an outer body that has a wall 2A constituting the raised surface 4a, and sidewalls 410, 410 extending from both respective edges of the wall 2A toward the back side 4b. The first recesses 400a are fitting holes formed in two respective sidewalls 410 each having a rectangular parallelepiped shape. These sidewalls 410 protrude substantially perpendicularly to the back surface 2Ab opposite to the raised surface 4a of the brush member 2 while facing each other across the specific region 4c. That is, the two sidewalls 410 are provided with the respective filling holes in their surfaces facing each other. The first protrusions 400b are columnar protrusions protruding substantially perpendicularly to respective sidewalls 411 formed by cutting away both ends of a leading end portion of the brush member 2 to a size that allows the leading end portion of the brush member 2 to be inserted between the sidewalls 410. The sidewalls 410 serve to guide the brush member 2 when the brush member 2 is attached to the main body 1 along the longitudinal direction of the main body 1.

FIGS. 7A and 8A each illustrate a state just before the first positioning elements (first recesses 400a) provided in the main body 1 are fitted with the respective second positioning elements (first protrusions 400b) provided in the end portion B of the brush member 2 after the stem 6 of the main body 1 is inserted into the brush member 2 from the end portion B thereof. FIGS. 7B and 8B each illustrate a state where the first positioning elements (first recesses 400a) provided in the main body 1 are fitted with the respective second positioning elements (first protrusions 400b) provided in the other end portion B of the brush member 2. In this state, the light emitting part 50 and the light receiving part 51, provided on the main body 1, and the specific region 4c are positioned so as to overlap with each other in the longitudinal direction of the main body 1.

While a recessed shape is used as the first positioning element and a protruding shape is used as the second positioning element in the present modification, the present invention is not limited thereto. For example, a protruding shape may be used as the first positioning element, and a recessed shape may be used as the second positioning element. Even this case enables obtaining a similar effect to that of the present modification.

(Modification 2)

Figure 10A:
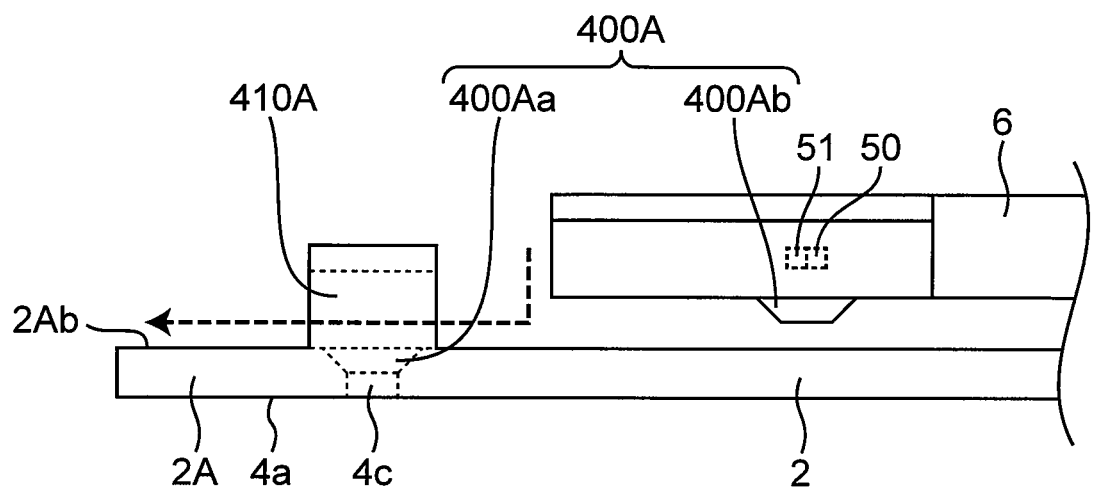
FIG. 10A is a side view of FIG. 9A.

In place of the positioning structure 400 according to the modification 1 described above, a positioning structure 400A as illustrated in FIG. 10A may be provided.

Figure 9A:
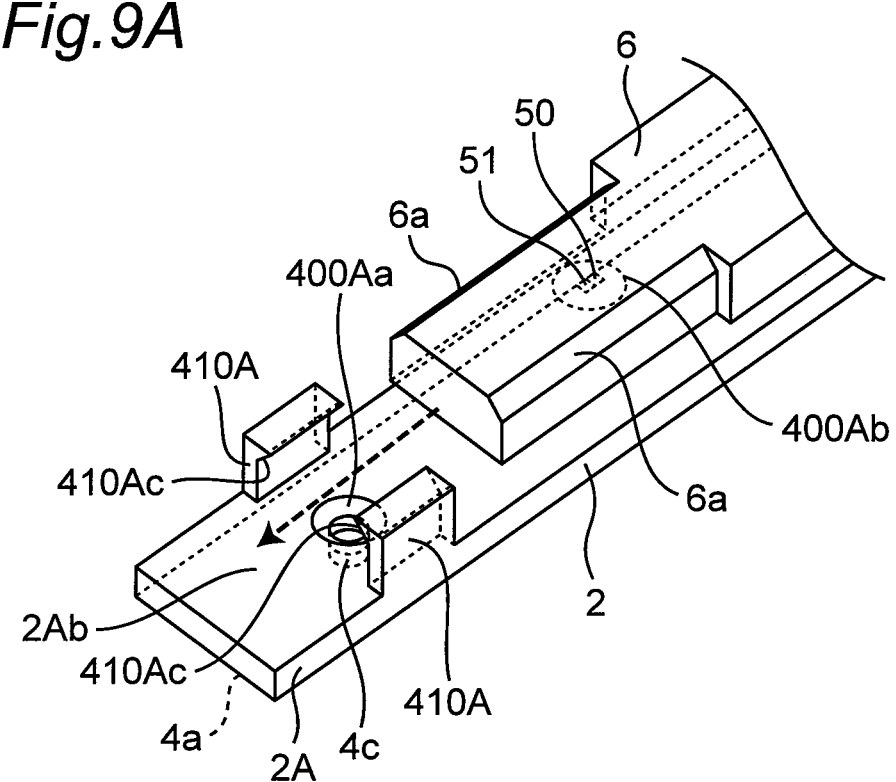
FIG. 9A is a schematic view for illustrating a first state of operation of a positioning structure 400A according to a modification 2 of the embodiment of the present invention.
Figure 9B:
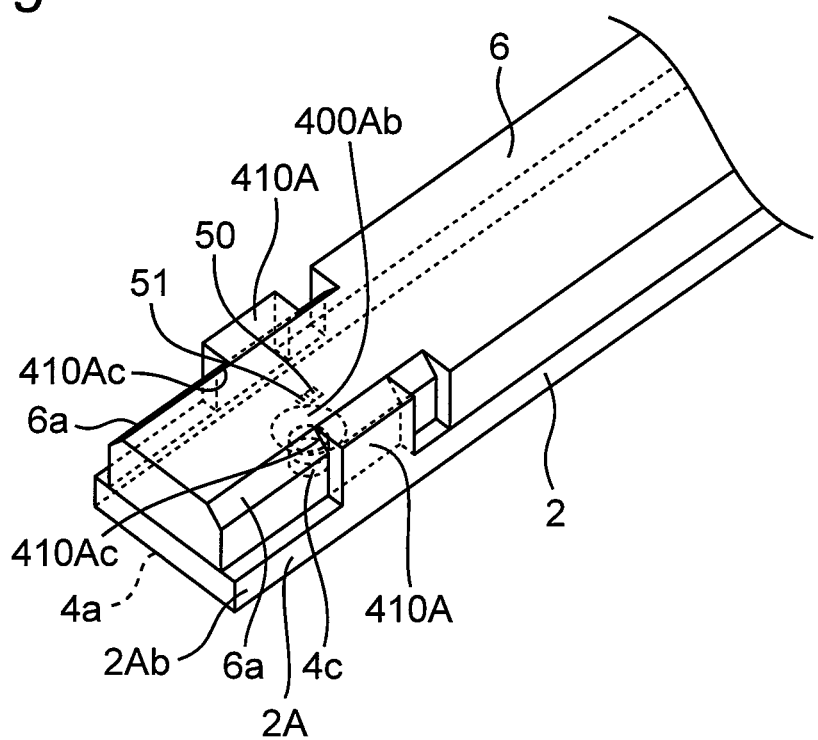
FIG. 9B is a schematic view for illustrating a second state of operation of the positioning structure 400A according to the modification 2 of the embodiment of the present invention.
Figure 10B:
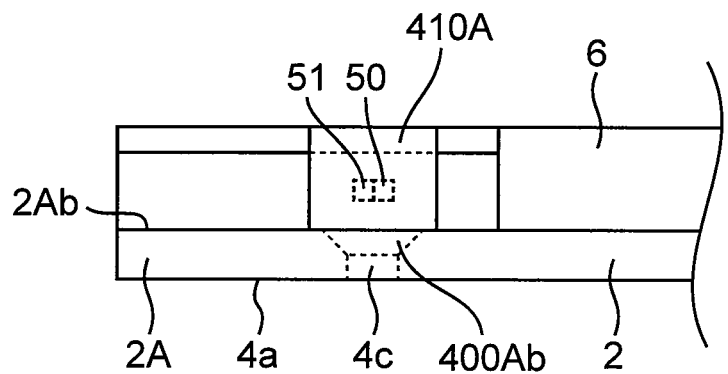
FIG. 10B is a side view of FIG. 9B.

FIGS. 9A and 9B are each a schematic view for illustrating operation of the positioning structure 400A according to the modification 2 of the embodiment of the present invention. FIG. 10A is a side view of FIG. 9A, and FIG. 10B is a side view of FIG. 9B. The positioning structure 400A includes a first positioning element (second recess 400Aa) provided in a surface opposite to the raised surface 4a, and a second positioning element (second protrusion 400Ab) provided in a leading end portion of the main body 1, and is configured such that the first positioning element can engage with the second positioning element.

FIGS. 9A and 10A each illustrate a state just before the first positioning element (second recess 400Aa) provided in the main body 1 is fitted with the second positioning element (second protrusion 400Ab) provided in the end portion B of the brush member 2 after the stem 6 of the main body 1 is inserted into the brush member 2 from the other end portion B thereof. FIGS. 9B and 10B each illustrate a state where the first positioning element (second recess 400Aa) provided in the main body 1 is fitted with the second positioning element (second protrusion 400Ab) provided in the end portion B of the brush member 2. In this state, the light emitting part 50 and the light receiving part 51, provided on the main body 1, and the specific region 4c are positioned so as to overlap with each other in the longitudinal direction of the main body 1. This allows the brush member 2 to be more easily fitted onto the main body 1 when the light emitting part 50 and the light receiving part 51 are positioned in the specific region 4c, thereby further facilitating attachment of the brush member 2 to the main body 1.

As illustrated in FIG. 9A, the head section 4 includes an outer body that has a wall 2A constituting the raised surface 4a, and sidewalls 410A, 410A extending from both respective edges of the wall 2A toward the back side 4b. The second recess 400Aa is a fitting hole provided on the back surface 2Ab opposite to the raised surface 4a of the brush member 2. The second recess 400Aa is disposed to overlap with the specific region 4c along the thickness direction of the brush member 2. The second protrusion 400Ab is a protrusion provided on a surface of the stem 6 of the main body 1, being in contact with the brush member 2. The second protrusion 400Ab is disposed to overlap the light emitting part 50 and the light receiving part 51 along the thickness direction of the main body 1.

There are provided two sidewalls 410A each having a rectangular parallelepiped shape. These sidewalls 410A protrude substantially perpendicularly to the back surface 2Ab opposite to the raised surface 4a of the brush member 2 while facing each other across the second recess 400Aa. The sidewalls 410A are provided in their upper ends (in FIG. 9A) with respective inclined surfaces 410Ac that are inclined in an overhanging manner in a direction approaching each other. Meanwhile, there are provided cutout surfaces 6a each inclined corresponding to the inclined surface 410Ac of the sidewall 410A, on both respective sides of a top face (in FIG. 9A) of the leading end portion of the stem 6. Accordingly, the sidewalls 410A serve to guide the brush member 2 when the brush member 2 is attached to the main body 1 along the longitudinal direction of the main body 1. In addition, the inclined surfaces 410Ac of the respective sidewalls 410A, which work as holding portions, hold the leading end portion of the stem 6 in a state where the brush member 2 is attached to the main body 1, so that structural strength of the toothbrush as a whole increases.

While a recessed shape is used as the first positioning element and a protruding shape is used as the second positioning element in the present modification, the present invention is not limited thereto. For example, a protruding shape may be used as the first positioning element, and a recessed shape may be used as the second positioning element. Even this case enables obtaining a similar effect to that of the present modification.

While the embodiment and modifications described above each allow light to pass through the specific region 4c, the present invention is not limited thereto. For example, it may be configured to input and output invisible light, heat, electrical stimulation, ultrasonic vibration, liquid, gas, or powder.

As is described above, a toothbrush of the present disclosure comprises:

a main body having a shape elongated in one direction; and a replacement brush having a cylindrical shape and attached to an end portion of the main body in a longitudinal direction, the end portion of the main body having a stem projecting in the longitudinal direction, the replacement brush including a head section having a raised surface provided with bristles erected, and a neck section that is fitted and attached around the stem of the main body, along the longitudinal direction of the main body to be attached, wherein the head section is opened in a back side opposite to the raised surface to form a cavity, and the cavity communicates with a space in the neck section, the head section includes an outer body that has a wall constituting the raised surface, and sidewalls extending from both respective edges of the wall toward the back side, the stem extends to a back surface of the wall constituting the raised surface through a space inside the neck section when the replacement brush is attached to the end portion of the main body, each of the sidewalls of the head section has a leading end provided with a holding portion for holding the stem of the main body, and the neck section includes a disengaging prevention structure for preventing the end portion attached of the main body from disengaging.

The description of "the replacement brush", wherein "the head section is opened in a back side opposite to the raised surface", includes the replacement brush having a plate-like shape. In the present specification, the "end portion" is not limited to each end itself, and may indicate a portion within a certain range.

The toothbrush of the present disclosure includes the head section having a raised surface provided with bristles erected, and the neck section that is fitted and attached around the end portion of the main body, along the longitudinal direction of the main body to be attached. The head section is opened in a back side opposite to the raised surface to form a cavity, and the cavity communicates with a space in the neck section.

Thus, when the replacement brush is attached to the main body, the head section of the replacement brush excluding the bristles has a thickness less than that of the neck section of the replacement brush. This enables the head section to be reduced in thickness to less than that of a conventional one, so that a user can easily insert the head section of the toothbrush into its mouth and brushing of its back teeth can be facilitated. In addition, the head section is opened in a back side opposite to the raised surface, so that the head section has a volume less than that of the head section having a cylindrical shape. As a result, material costs can be reduced compared with conventional material costs. The head section of the replacement brush is opened to form a cavity, and the cavity communicates with a space in the neck section, so that water can pass through the inside of the replacement brush in a cylindrical shape through the head section and the neck section. Thus, as compared with the case that the head section is not opened, the inside of the replacement brush can be easily cleaned. In addition, the head section of the replacement brush is opened, so that the replacement brush is reduced in weight to enable reduction in power consumption by efficiently transmitting output of a motor to the replacement brush. In this toothbrush, holding portions provided at the leading ends of the sidewalls hold the stem of the main body in a state where the replacement brush is attached to the end portion of the main body, so that structural strength of the toothbrush as a whole increases.

Further, in the toothbrush of the present disclosure, the neck section is provided with the disengaging prevention structure for preventing the end portion attached of the main body edge from disengaging. This enables the replacement brush to be prevented from disengaging from the main body even while a user is brushing its teeth.

In one embodiment of the toothbrush, the disengaging prevention structure includes a cutout portion provided at an end portion of a cylindrical peripheral wall of the neck section, on a side facing the main body, and a locking protrusion that is provided on a side surface of the main body and that is able to be fitted into the cutout portion.

The toothbrush of this embodiment includes a cutout portion provided at an end portion of the cylindrical peripheral wall of the neck section, on a side facing the main body, and a locking protrusion that is provided on a side surface of the main body and that can be fitted into the cutout portion. This enables the replacement brush to be reliably fixed to the main body by fitting the cutout portion and the locking protrusion to each other when the replacement brush is attached to the main body. As described above, the replacement brush can be reliably fixed to the main body, so that vibration from the main body can be efficiently and effectively transmitted to a brush portion of the replacement brush.

In another aspect, a toothbrush of the present disclosure comprises:

a main body having a shape elongated in one direction; and a replacement brush having a cylindrical shape and attached to an end portion of the main body in a longitudinal direction, the replacement brush including a head section having a raised surface provided with bristles erected, and a neck section that is fitted and attached around the end portion of the main body, along the longitudinal direction of the main body to be attached, wherein the head section is opened in a back side opposite to the raised surface, a light emitting part that is provided in the end portion of the main body to emit light to a tooth surface through a specific region in the raised surface; and a positioning structure for positioning the light emitting part in the end portion of the main body and the specific region so as to overlap with each other in the longitudinal direction of the main body when the replacement brush is attached to the main body.

It is desirable that the bristles are omitted in the "specific region" of the raised surface.

As described in connection with the former aspect, the toothbrush of this aspect enables the head section to be reduced in thickness to less than that of a conventional one, so that a user can easily insert the head section of the toothbrush into its mouth and brushing of its back teeth can be facilitated. In addition, the head section is opened in a back side opposite to the raised surface, so that the head section has a volume less than that of the head section having a cylindrical shape. As a result, material costs can be reduced compared with conventional material costs. In addition, the head section of the replacement brush is opened, so that the replacement brush is reduced in weight to enable reduction in power consumption by efficiently transmitting output of a motor to the replacement brush. The toothbrush of this aspect further enables a light emitting part in the main body and the specific region to be positioned so as to overlap with each other.

In one embodiment of the toothbrush, the positioning structure includes a first positioning element provided in a surface opposite to the raised surface of the brush, and a second positioning element provided in a leading end portion of the main body, and the first positioning element and the second positioning element are configured to engage with each other.

The toothbrush of this embodiment causes the light emitting part and the specific region to be less likely to be displaced from each other.

In one embodiment of the toothbrush, the first positioning element has any one of a recessed shape and a protruding shape, and the second positioning element has the recessed shape or the protruding shape that is different from a shape of the first positioning element.

The toothbrush of this embodiment allows the replacement brush to be easily fitted onto the main body when the light emitting part is positioned in the specific region, thereby further facilitating attachment of the replacement brush.

As is apparent from the above, the toothbrush of the present disclosure allows the toothbrush to be easily inserted into a mouth, and brushing of the back teeth to be facilitated.

The embodiment described above is an example, and various modifications are possible without departing from the scope of the present invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A toothbrush comprising:
a main body having a shape elongated in one direction; and
a replacement brush having a cylindrical shape and attached to an end portion of the main body in a longitudinal direction,
the end portion of the main body having a stem projecting in the longitudinal direction,
the replacement brush including a head section having a raised surface provided with bristles erected, and a neck section that is fitted and attached around the stem of the main body, along the longitudinal direction of the main body to be attached,
wherein the head section is opened in a back side opposite to the raised surface to form a cavity, and the cavity communicates with a space in the neck section,
the head section includes an outer body that has a wall constituting the raised surface, and sidewalls extending from both respective edges of the wall toward the back side,
the stem extends to a back surface of the wall constituting the raised surface through a space inside the neck section when the replacement brush is attached to the end portion of the main body,
each of the sidewalls of the head section has a leading end provided with a holding portion for holding the stem of the main body, and
the neck section includes a disengaging prevention structure for preventing the end portion attached of the main body from disengaging.

2. The toothbrush according to claim 1, wherein the disengaging prevention structure includes a cutout portion provided at an end portion of a cylindrical peripheral wall of the neck section, on a side facing the main body, and a locking protrusion that is provided on a side surface of the main body and that is able to be fitted into the cutout portion.

3. A toothbrush comprising:
a main body having a shape elongated in one direction; and
a replacement brush having a cylindrical shape and attached to an end portion of the main body in a longitudinal direction,
the replacement brush including a head section having a raised surface provided with bristles erected, and a neck section that is fitted and attached around the end portion of the main body, along the longitudinal direction of the main body to be attached,
wherein the head section is opened in a back side opposite to the raised surface,
a light emitting part that is provided in the end portion of the main body to emit light to a tooth surface through a specific region in the raised surface; and
a positioning structure for positioning the light emitting part in the end portion of the main body and the specific region so as to overlap with each other in the longitudinal direction of the main body when the replacement brush is attached to the main body.

4. The toothbrush according to claim 3, wherein
the positioning structure includes a first positioning element provided in a surface opposite to the raised surface of the brush, and a second positioning element provided in a leading end portion of the main body, and
the first positioning element and the second positioning element are configured to engage with each other.

5. The toothbrush according to claim 4, wherein
the first positioning element has any one of a recessed shape and a protruding shape, and
the second positioning element has the recessed shape or the protruding shape that is different from a shape of the first positioning element.

* * * * *